(12) United States Patent
Argent

(10) Patent No.: US 9,402,761 B2
(45) Date of Patent: Aug. 2, 2016

(54) DEVICE FOR USE WITH AN OSTOMY APPLIANCE

(75) Inventor: Peter Argent, Horsham (GB)

(73) Assignee: SALTS HEALTHCARE LIMITED, Horsham, West Sussex (GB)

( * ) Notice: Subject to any disclaimer, the term of this patent is extended or adjusted under 35 U.S.C. 154(b) by 0 days.

(21) Appl. No.: 13/120,579

(22) PCT Filed: Sep. 9, 2009

(86) PCT No.: PCT/GB2009/002164
§ 371 (c)(1),
(2), (4) Date: Mar. 23, 2011

(87) PCT Pub. No.: WO2010/034966
PCT Pub. Date: Apr. 1, 2010

(65) Prior Publication Data
US 2011/0172619 A1    Jul. 14, 2011

(30) Foreign Application Priority Data
Sep. 23, 2008  (GB) .................... 0817360.1

(51) Int. Cl.
*A61F 5/44* (2006.01)
*A61F 5/445* (2006.01)
*A61F 5/448* (2006.01)

(52) U.S. Cl.
CPC *A61F 5/445* (2013.01); *A61F 5/448* (2013.01)

(58) Field of Classification Search
USPC ........................................................ 604/339
See application file for complete search history.

(56) References Cited

U.S. PATENT DOCUMENTS

| 2,639,710 | A | * | 5/1953 | Fazio | A61F 5/448 604/342 |
| 3,495,592 | A | * | 2/1970 | Shepard | A61F 5/445 604/336 |
| 3,736,934 | A | * | 6/1973 | Hennessy | A61F 5/448 604/342 |
| 3,906,951 | A | * | 9/1975 | Chen | A61F 5/445 604/336 |
| 4,054,140 | A | * | 10/1977 | Etes | A61F 5/445 604/343 |
| 4,219,023 | A | * | 8/1980 | Galindo | A61F 5/445 604/344 |

(Continued)

FOREIGN PATENT DOCUMENTS

| DE | 20012498 | 1/2001 |
| GB | 2041753 | 9/1980 |

(Continued)

OTHER PUBLICATIONS

UK Search Report for Application No. GB0817360.1 mailed on Jan. 9, 2009.

(Continued)

*Primary Examiner* — Tatyana Zalukaeva
*Assistant Examiner* — Guy K Townsend
(74) *Attorney, Agent, or Firm* — Shaukat A. Karjeker; Carstens & Cahoon, LLP

(57) ABSTRACT

A device (10) for use with an ostomy appliance, the device (10) having an opening (12), surrounded by a peripheral wall (13), to receive a stoma, and a flange part (14) connected to the peripheral wall (13), which flange part (14) extends substantially perpendicularly away from the opening (12).

13 Claims, 4 Drawing Sheets

(56) References Cited

U.S. PATENT DOCUMENTS

| | | | | |
|---|---|---|---|---|
| 4,222,923 A * | 9/1980 | Rhodes | A61L 24/043 | 524/169 |
| 4,231,369 A * | 11/1980 | Sorensen | A61F 5/443 | 604/336 |
| 4,292,972 A * | 10/1981 | Pawelchak | A61L 15/60 | 264/50 |
| 4,538,603 A * | 9/1985 | Pawelchak | A61F 13/02 | 424/447 |
| 4,551,490 A * | 11/1985 | Doyle | A61L 15/585 | 428/355 BL |
| 4,610,676 A * | 9/1986 | Schneider | A61F 5/448 | 604/339 |
| 4,610,677 A * | 9/1986 | Mohiuddin | A61F 5/448 | 604/339 |
| 4,775,374 A * | 10/1988 | Cilento | A61F 5/443 | 604/338 |
| 4,846,798 A * | 7/1989 | Holtermann | A61F 5/448 | 604/339 |
| 4,889,534 A * | 12/1989 | Mohiuddin | A61F 5/448 | 604/339 |
| 4,973,323 A * | 11/1990 | Kaczmarek | A61F 5/448 | 604/277 |
| 5,009,224 A * | 4/1991 | Cole | A61L 15/58 | 128/887 |
| 5,074,852 A * | 12/1991 | Castellana | A61F 5/443 | 604/336 |
| 5,147,340 A * | 9/1992 | Lavender | A61F 5/448 | 604/332 |
| 5,147,698 A * | 9/1992 | Cole | A61L 15/58 | 428/317.3 |
| 5,312,381 A * | 5/1994 | Brooks | A61F 5/448 | 604/332 |
| 5,364,379 A * | 11/1994 | Ozenne | F16L 37/008 | 604/342 |
| 5,545,154 A * | 8/1996 | Oberholtzer | A61F 5/443 | 604/336 |
| 5,834,009 A * | 11/1998 | Sawers | A61F 5/443 | 424/443 |
| 5,947,942 A * | 9/1999 | Galjour | A61F 5/449 | 604/345 |
| 6,520,943 B1 * | 2/2003 | Wagner | A61F 5/443 | 604/332 |
| 6,740,067 B2 * | 5/2004 | Leise, Jr. | A61F 5/448 | 604/332 |
| 7,087,042 B2 * | 8/2006 | Montgomery | A61F 5/448 | 604/277 |
| 7,172,581 B2 * | 2/2007 | Ciok | A61F 5/445 | 604/336 |
| 7,192,420 B2 * | 3/2007 | Whiteford | A61F 5/448 | 604/332 |
| 7,214,217 B2 * | 5/2007 | Pedersen | A61F 5/448 | 604/332 |
| 2004/0039357 A1 * | 2/2004 | Andersen | A61F 5/448 | 604/332 |
| 2005/0033249 A1 | 2/2005 | Whiteford | | |

FOREIGN PATENT DOCUMENTS

| | | |
|---|---|---|
| GB | 2422112 | 7/2006 |
| GB | 2425482 | 11/2006 |
| WO | 98/53771 | 12/1998 |
| WO | 99/60959 | 12/1999 |
| WO | 02/15827 | 2/2002 |
| WO | 2004/062536 | 7/2004 |
| WO | 2004/069117 | 8/2004 |

OTHER PUBLICATIONS

PCT International Search Report for PCT Application No. PCT/GB2009/002164 mailed on Nov. 10, 2009.

* cited by examiner

DEVICE FOR USE WITH AN OSTOMY APPLIANCE

BACKGROUND OF THE INVENTION

The invention relates to a device for use with an ostomy appliance.

More particularly, this invention relates to a device intended to surround a stoma of a user. A stoma is a surgically constructed tube of a user's digestive tract that protrudes through a user's skin and allows for waste to be collected therefrom.

DESCRIPTION OF THE PRIOR ART

It is known to provide a user with an ostomy appliance including a pouch which has an opening to receive the stoma. A body-side portion of the pouch is provided with an adhesive member for adhering the pouch to a user's skin surrounding the stoma. In use, waste from the user's digestive tract is expelled through the stoma and is collected in the pouch. The user then either replaces the pouch or drains the collected waste from the pouch (if the pouch provides for such draining—usually by the provision of a resealable aperture at a lower part of the pouch).

One common problem with known ostomy pouches is that if a good seal around the stoma is not provided leaks can occur which can cause damage to the skin around the user's stoma. This can result in irritation and great discomfort to the user.

SUMMARY OF THE INVENTION

It is an object of the present invention to address the above problem.

Therefore, according to a first aspect of the present invention, we provide a device for use with an ostomy appliance, the device having an opening, surrounded by a peripheral wall, to receive a stoma, and a flange part connected to the peripheral wall, which flange part extends substantially perpendicularly away from the opening.

The peripheral wall may be elastically deformable, so as to provide, in use, a fluid-tight seal between the wall and the user's stoma.

The peripheral wall and the flange may be formed as a one-piece component.

The peripheral wall may be substantially cylindrical, and the flange part may extend substantially radially outwardly away from the peripheral wall.

The peripheral wall may taper towards an axis of the opening as it extends away from the flange part. The taper may be at an angle of 6° to the axis of the opening.

The peripheral wall and the flange part may be connected by a curved portion.

The flange part may be substantially annular.

The flange part may be sandwiched between a first adhesive member and a second adhesive member.

The first adhesive member may be adapted for adhering to skin surrounding a user's stoma.

The second adhesive member may be adapted for adhering to a pouch to receive waste from the stoma.

The first adhesive member may be a hydrocolloid material.

The first and second adhesive members may be covered by removable cover members.

The device may be manufactured from a polyurethane or latex material.

The peripheral wall may be less than or equal to 0.2 mm in thickness.

The peripheral wall may not be more than 30 mm in length.

The peripheral wall may be between 8 mm and 20 mm in length.

According to a second aspect of the invention, we provide an ostomy appliance including a device according to the first aspect of the invention.

The device according to the first aspect of the invention may be connected to an internal surface of a pouch of the ostomy appliance.

The device according to the first aspect of the invention may be connected to an external surface of a pouch of the ostomy appliance.

BRIEF DESCRIPTION OF THE DRAWINGS

Embodiments of the invention will now be described by way of example only with reference to the accompanying drawings, of which.

DETAILED DESCRIPTION OF THE PREFERRED EMBODIMENTS

Figure 1:
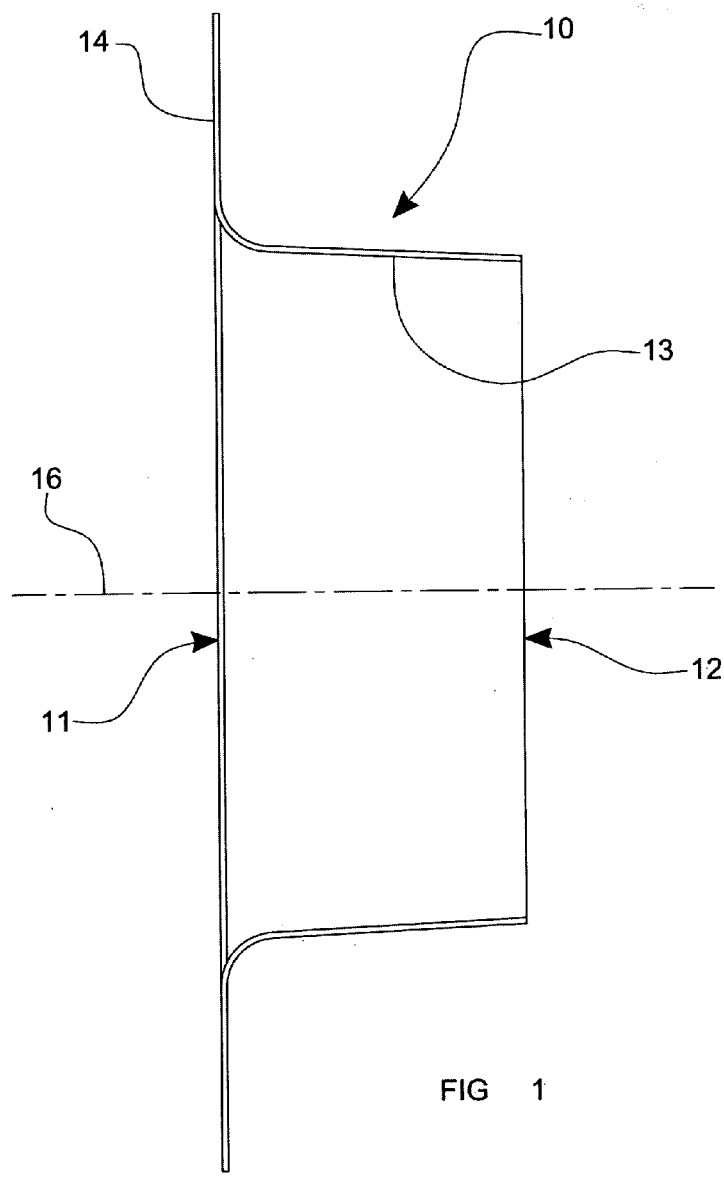
FIG. 1 is a side cross-sectional view of a device for use with an ostomy appliance in accordance with the first aspect of the invention.
Figure 2:
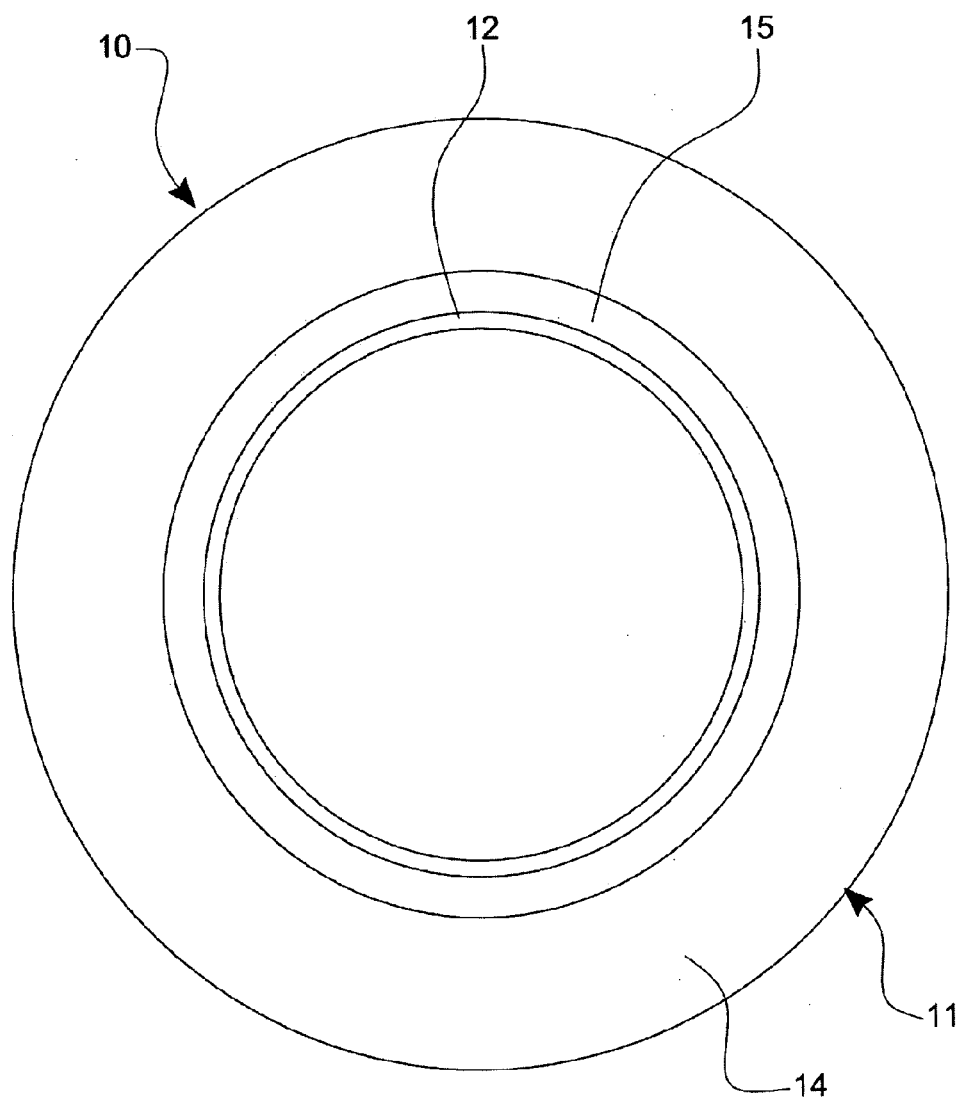
FIG. 2 is a plan view of the device of FIG. 1.

Referring to FIGS. 1 and 2 there is shown a device 10 for use with an ostomy appliance. The device 10 has an opening 12, surrounded by a substantially cylindrical peripheral wall 13 which in this example is less than or equal to 0.2 mm in thickness. In use, and discussed in more detail below, the opening 12 receives a stoma (not shown). The device 10 also includes an annular flange part 14 which is connected to and extends substantially perpendicularly away from one end of the peripheral wall 13. The flange part 14 extends substantially radially away from an axis 16 of the opening.

The flange part 14 and the peripheral wall 13 are connected by a curved portion 15 which extends away from the axis 16 of the opening 12 as it extends from the peripheral wall 13 to the flange part 14. The curved portion 15 between the peripheral wall 13 and the flange part 14 assists a user in centering the opening 12 over their stoma.

In this example, the peripheral wall 13 tapers towards the axis 16 of the opening 12 as it extends away from the flange part 14. This aids in providing an interference, fluid-tight, seal between the peripheral wall 13 and the user's stoma. As an example, the internal diameter of the opening 12 should be selected such that it is 3 mm to 6 mm smaller than the external diameter of the user's stoma, as this provides for an adequate interference, fluid-tight, seal. It has been found that the following dimensions are appropriate for use:

| External Diameter of User's Stoma (mm) | Internal Diameter of Opening 12 (mm) |
| --- | --- |
| 20.0 to 23.0 | 17.00 |
| 23.0 to 26.0 | 20.00 |
| 26.0 to 29.0 | 23.00 |

| External Diameter of User's Stoma (mm) | Internal Diameter of Opening 12 (mm) |
|---|---|
| 29.0 to 32.0 | 26.00 |
| 32.0 to 35.9 | 29.00 |
| 35.0 to 38.0 | 32.00 |

In the present example, the taper is at an angle of 6°, but is must be appreciated that other angles of taper could be utilised. In addition, the tapering of the peripheral wall 13 provides for compact storage of one or more like devices 10, as they can be stacked one on top of each other, with the peripheral wall 13 of one device 10 received in the opening 12 of an adjacent device 10.

In the present example, the device 10 is manufactured as a one-piece component using a moulding process, for example, injection moulding or dip forming. It should be appreciated, however, that any other appropriate forming process can be used.

The device 10 is manufactured from a polyurethane material (e.g. that known as Alphathane™) and is, as a result, elastically deformable. This material property is essential for the device 10, as it ensures a fluid-tight fit with a user's stoma. It should be appreciate that other materials could be used so long as they provide for adequate elastic deformation of the opening 12.

The device 10 can be used as an additional component to many existing ostomy appliances to provide a seal around the user's stoma so as to prevent leakage and contact of collected waste with the user's skin. A user simply positions the device 10 over their stoma, so that a fluid-tight seal is provided therebetween and so that the external surface of the stoma is covered by the peripheral wall 13. The user then attaches the ostomy appliance to their skin as they would normally do so. An adhesive flange, conventionally provided as part of the ostomy appliance, adheres both to the user's skin and to the external surface of the flange part 14 of the device, thus securing the device 10 relative to the pouch. If it is desired to remove the appliance, e.g. for emptying or to replace with a fresh appliance, the user can either re-use the device 10 or install a fresh device 10.

As an alternative, the device 10 may be provided already connected to an adhesive member. For example, a surface of the flange part 14 which faces the user's skin may be connected to or provided with an annular hydrocolloid adhesive member, by adhesion, heat welding or any other appropriate means. It is important to ensure that the aperture in the adhesive member is larger than the opening 12 of the device 10, thus permitting the opening 12 to stretch during installation.

Figure 3:
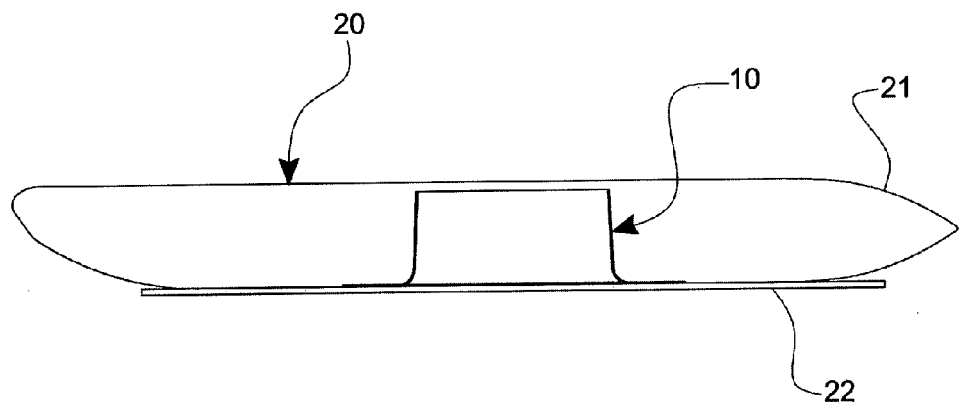
FIG. 3 is a side cross-sectional view of a first embodiment of an ostomy appliance in accordance with the second aspect of the invention, including a device in accordance with the first aspect of the invention.
Figure 4:
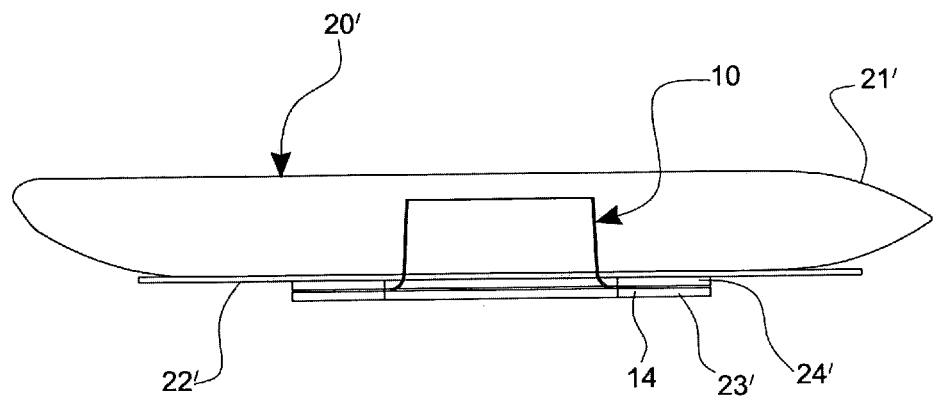
FIG. 4 is a side cross-sectional view of a second embodiment of an ostomy appliance in accordance with the second aspect of the invention, including a device in accordance with the first aspect of the invention.

Referring to FIGS. 3 and 4, these show first and second embodiments of a second aspect of the invention—where the device 10 has been incorporated as an integral component of an ostomy appliance 20, 20'.

In FIG. 3 the ostomy appliance 20 includes a pouch 21, to receive waste, and a body side flange 22, connected to the pouch 21, for connection to a user. The flange 22 can be connected to a user by any known means, e.g. by an adhesive or by a coupling device. The appliance 20 includes a device 10 (as described and shown in FIGS. 1 and 2) which is positioned inside the pouch 21 so that the opening 12 of the device 10 is aligned with an opening to the pouch 21. A surface of the flange part 14 remote from the peripheral wall 13 is connected to an internal surface of the pouch 21, e.g. by an adhesive, heat welding or any other appropriate means. By providing an ostomy appliance 21 with an integral device 10 to surround the stoma renders the appliance user-friendly, as a user only needs to position one component relative to their stoma—namely to position the opening to the pouch 21 over their stoma.

As an alternative to the configuration shown in FIG. 3, a surface of the flange part 14 adjacent the peripheral wall 13 may be connected to an external surface of the body side flange 22 of the pouch 21, e.g. by an adhesive, heat welding or any other appropriate means.

FIG. 4 shows a second embodiment of an ostomy appliance 20', which also includes a device 10. In this example, the flange part 14 of the device 10 is sandwiched between a first adhesive member 23' and a second adhesive member 24'. The first adhesive member 23' is adapted for adhering to skin surrounding a user's stoma, and is preferably manufactured from a hydrocolloid material. The second adhesive member 24' is adhered to an external surface of the body side flange 22' (e.g. by an adhesive, heat welding or any other appropriate means), so that the opening 12 of the device 10 is aligned with an opening to the pouch 21', through the body side flange 22'. Again, by providing an ostomy appliance 21' with an integral device 10 to surround the stoma renders the appliance 21' user-friendly, as a user only needs to position one component relative to their stoma.

It should be appreciated that the device 10 of FIGS. 1 and 2 could be supplied as a single component (i.e. not already connected to the body side flange 22 of the pouch 21) having the first and second adhesive members 23', 24' connected thereto (as shown in FIG. 4). The device 10 would, preferably, be also provided with removable cover members covering the adhesive surfaces 23', 24'. Such a configuration can be used with many known ostomy appliances, thus providing users of those appliances with the advantages associated with the device 10—namely forming a seal around the stoma to prevent leakage and contact of collected waste with the user's skin.

For the avoidance of doubt, the device 10 can also be utilised with a two-piece ostomy appliances (i.e. appliances which have two mating fixings, one which remains connected to the user's skin and the other of which is connected to the pouch).

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. A device for use with an ostomy appliance, the device comprising:
   an opening, surrounded by a substantially cylindrical peripheral wall, to receive a stoma; and
   a flange part connected to the peripheral wall, which flange part extends substantially perpendicularly away from the opening;
   wherein an inner surface of the peripheral wall tapers toward an axis of the opening as it extends away from the flange part, and the peripheral wall and the flange part are connected by a curved portion extending in the direction of the axis of the opening, and wherein the peripheral wall is elastically deformable and the inner surface of the peripheral wall, between and including the curved portion and a proximal end of the wall, is configured to elastically deform on engagement with the stoma of the user to provide a fluid-tight adhesive-free seal between the wall and the stoma; and wherein the peripheral wall and the flange are formed as a one-piece component.

2. A device according to claim 1 wherein the flange part extends substantially radially outwardly away from the peripheral wall.

3. A device according to claim 1 wherein the taper at an angle of 6° to an axis of the opening.

4. A device according to claim 1 wherein the flange part is substantially annular.

5. A device according to claim 1 wherein the flange part is sandwiched between a first adhesive member and a second adhesive member.

6. A device according to claim 5 wherein the first adhesive member is adapted for adhering to skin surrounding a user's stoma.

7. A device according to claim 5 wherein the second adhesive member is adapted for adhering to a pouch to receive waste from the stoma.

8. A device according to claim 5 wherein the first adhesive member is a hydrocolloid material.

9. A device according to claim 5 wherein the first and second adhesive members are covered by removable cover members.

10. An ostomy appliance including a device according to claim 1.

11. An ostomy appliance according to claim 10 wherein the device is connected to an internal surface of a pouch of the ostomy appliance.

12. An ostomy appliance according to claim 10 wherein the device is connected to an external surface of a pouch of the ostomy appliance.

13. A device for use with an ostomy appliance, the device comprising:

an opening, surrounded by a substantially cylindrical peripheral wall, to receive a stoma; and a flange part connected to the peripheral wall, which flange part extends substantially perpendicularly away from the opening;

wherein an inner surface of the peripheral wall tapers toward an axis of the opening as it extends away from the flange part, and the peripheral wall and flange part are connected by a curved portion extending in the direction of the axis of the opening, and wherein the peripheral wall is elastically deformable and the inner surface of the peripheral wall, between and including the curved portion and a proximal end of the wall, is configured to elastically deform on engagement with a stoma of the user and provides an interference, fluid-tight adhesive-free seal between the wall and the stoma; and wherein the peripheral wall and the flange are formed as a one-piece component.

* * * * *